United States Patent [19]

Greenquist

[11] Patent Number: 4,461,829

[45] Date of Patent: Jul. 24, 1984

[54] HOMOGENEOUS SPECIFIC BINDING ASSAY ELEMENT AND LYOPHILIZATION PRODUCTION METHOD

[75] Inventor: Alfred C. Greenquist, Elkhart, Ind.

[73] Assignee: Miles Laboratories, Inc., Elkhart, Ind.

[21] Appl. No.: 302,218

[22] Filed: Sep. 14, 1981

[51] Int. Cl.$^3$ .................... G01N 33/54; G01N 33/52; G01N 33/58
[52] U.S. Cl. .......................................... 435/7; 422/56; 435/177; 435/188; 435/805; 436/530; 436/810
[58] Field of Search ...................... 435/4, 7, 177, 188, 435/805, 810; 23/230 B; 422/55-58; 424/8, 12; 252/408; 436/530, 810

[56] References Cited

U.S. PATENT DOCUMENTS

| | | | |
|---|---|---|---|
| 3,905,767 | 9/1975 | Morris et al. | 23/230 B |
| 4,017,597 | 4/1977 | Reynolds | 435/7 |
| 4,059,407 | 11/1977 | Hochstrasser | 435/7 |
| 4,094,647 | 6/1978 | Deutsch et al. | 435/805 X |
| 4,230,797 | 10/1980 | Boguslaski et al. | 435/810 X |
| 4,258,001 | 3/1981 | Pierce et al. | 435/7 |
| 4,260,392 | 4/1981 | Lee | 435/805 X |
| 4,279,992 | 7/1981 | Boguslaski et al. | 435/7 |
| 4,299,916 | 11/1981 | Litman et al. | 435/7 |

OTHER PUBLICATIONS

Watzek, "*Immunochemical Method for Determining Antigens and Antibodies in Biological Fluids*", Chemical *Abstracts*, vol. 86, No. 17, p. 225, (1977), Abst. No. 117285p.

*Primary Examiner*—Sidney Marantz
*Attorney, Agent, or Firm*—Edward H. Gorman, Jr.

[57] ABSTRACT

A homogeneous specific binding assay element, a method for its preparation, and a method for its use in determining a ligand in or the ligand binding capacity of a liquid sample are disclosed. The test element comprises a solid carrier incorporated with reagents for a homogeneous specific binding assay system which produces a detectable response, usually an electromagnetic radiation signal, that is a function of the presence or amount of the liquid in or the ligand binding capacity of the sample. There is further disclosed a method for preparing a homogeneous specific binding assay element for determining a ligand in or the ligand binding capacity of a liquid sample by incorporating a carrier with a composition which includes a label conjugate, comprising a label component coupled to a ligand moiety or a specific binding analog thereof, and a reagent reactive with the label conjugate, which method comprises (a) incorporating the carrier with the reagent reactive with the label conjugate in a first liquid; (b) subjecting the carrier of (a) to conditions effective to reversibly suspend or reduce the activity of the reagent therein; (c) incorporating the carrier of (b) with the label conjugate; (d) subjecting the carrier of (c) to a temperature effective to freeze the reagent reactive with the label conjugate and the label conjugate; and (e) lyophilizing the reagent and label conjugate in the carrier of (d).

12 Claims, No Drawings

HOMOGENEOUS SPECIFIC BINDING ASSAY ELEMENT AND LYOPHILIZATION PRODUCTION METHOD

BACKGROUND OF THE INVENTION

1. Field of the Invention

This invention relates to test devices or elements, their preparation and their use in determining a ligand in or the ligand binding capacity of a liquid sample based on a specific binding assay, e.g., immunoassay principle. In particular, this invention relates to solid state carrier elements incorporated with homogeneous specific binding assay reagents.

2. Brief Description of the Prior Art

Test devices in the form of test strips and similar solid state analytical elements have become commonplace in the analysis of various types of samples, particularly biological fluids. Test strips designed for detecting clinically significant substances in biological fluids, such as serum and urine, have been advantageous in the diagnosis of disease.

Test strips of various types have been known and used for many years in a wide variety of fields, from the most familiar pH test paper devices to in vitro diagnostic devices for the detection of various urine and blood components such as glucose, protein, occult blood and so forth (e.g., as described in U.S. Pat. Nos. 3,164,534; 3,485,587; and 3,012,976). Reagent compositions found in such conventional test strips interact with the constituent or constituents to be determined by direct chemical reaction and, for this and other reasons, have limited sensitivity, being applied to the detection of substances that are present in liquid samples at concentrations in the millimolar range or above.

On the other hand, the development of specific binding assay techniques has provided useful analytical methods for determining various organic substances of diagnostic, medical, environmental and industrial importance which appear in liquid mediums at very low concentrations. Specific binding assays are based on the specific interaction between the ligand, i.e., the bindable analyte under determination, and a binding partner therefor. Where one of the ligand and its binding partner is an antibody and the other is a corresponding hapten or antigen, the assay is known as an immunoassay.

In conventional specific binding assay techniques, a sample of the liquid medium to be assayed is combined with various reagent compositions. Such compositions include a label conjugate comprising a binding component incorporated with a label. The binding component in the label conjugate participates with other constituents, if any, of the reagent composition and with the ligand in the medium under assay. This forms a binding reaction system in which two species, a bound-species and a free-species, of the label conjugate are formed. In the bound-species, the binding component of the label conjugate is bound by a corresponding binding partner, e.g., an antibody, whereas in the free-species, the binding component is not so bound. The relative amount or proportion of the label conjugate that results in the bound-species compared to the free-species is a function of the presence (or amount) of the ligand to be detected in the test sample.

Where the label conjugate in the bound-species is essentially indistinguishable in the presence of the label conjugate in the free-species by the means used to monitor the label, the bound-species and the free-species must be physically separated in order to complete the assay. This type of assay is referred to in the art as "heterogeneous". Where the bound-species and free-species forms of the label conjugate can be distinguished in the presence of each other, the separation step can be avoided, and the assay is said to be "homogeneous".

The first discovered type of highly sensitive specific binding assay was the radioimmunoassay which employs a radioactive isotope as the label. Such an assay necessarily must follow the heterogeneous format since the monitorable character of the label is qualitatively unchanged in the free- and bound-species. Because of the inconvenience and difficulty of handling radioactive materials and the necessity of a separation step, homogeneous assay systems have been devised using materials other than radioisotopes as the label component, including enzymes, bacteriophages, metals and organometallic complexes, coenzymes, enzyme substrates, enzyme activators and inhibitors, cycling reactants, organic and inorganic catalysts, prosthetic groups, chemiluminescent reactants, and fluorescent molecules. Such homogeneous specific binding assay systems provide a detectable response, e.g., an electromagnetic radiation signal, such as chemiluminescence, fluorescence emission, or color change, related to the present or amount of the ligand under assay in the liquid sample.

Commercially available test means for performing specific binding assays are usually in the form of test kits comprising a packaged combination of containers holding solutions or rehydratable compositions of the reagents necessary for carrying out the assay. To perform the actual assay method, aliquots of such solutions must be manually or instrumentally dispensed into a reaction vessel with the sample. If manually dispensed, the assay consequently requires the time and skill of a technician, and if instrumentally dispensed, the assay consequently requires the expense and maintenance of dispensing apparatus.

Solid phase test devices have been applied to heterogeneous specific binding assays in attempts to overcome the inconveniences and disadvantages of the requisite separation step. A commonly used solid phase device of this type comprises a nonporous surface, such as the interior surface of a test tube or other vessel, to which antibody is affixed or coated by adsorption or covalent coupling. U.S. Pat. Nos. 3,826,619; 4,001,583; 4,017,597; and 4,105,410 relate to the use of antibody coated test tubes in radioimmunoassays. Solid phase test devices have also been used in heterogeneous enzyme immunoassays (U.S. Pat. Nos. 4,016,043 and 4,147,752) and in heterogeneous fluorescent immunoassays (U.S. Pat. Nos. 4,025,310 and 4,056,724; and British Patent Spec. No. 1,552,374).

The use of such heterogeneous specific binding assay test devices is exemplified by the method of U.S. Pat. No. 4,135,884 relating to a so-called "gamma stick". The test device is incorporated with the antibody reagent and is brought into contact with the liquid sample and with the remaining reagents of the reaction system, principally the label conjugate. After an incubation period, the solid phase device is physically removed from the reaction solution and the label measured either in the solution or on the test device.

Similar devices where the antibody reagent is entrapped in a matrix such as a gel or paper web are described in U.S. Pat. Nos. 3,925,017; 3,970,429; 4,138,474;

3,966,897; 3,981,981 and 3,888,629 and in German OLS No. 2,241,646. Likewise, devices for use in hetergeneous specific binding assays wherein the antibody reagent is fixed to a matrix held in a flowthrough column are know (U.S. Pat. Nos. 4,036,947; 4,039,652; 4,059,684; 4,153,675; and 4,166,102). The test device is usually incorporated with less than all of the necessary reagents for carrying out the assay and is merely a means for rendering more convenient and necessary separation step.

Finally, heterogeneous specific binding assay test devices have been described wherein most or all of the necessary reagents are incorporated with the same carrier element, and wherein reagent/sample contacts and separation of the free- and bound-phases are accomplished by capillary migrations along the carrier element (U.S. Pat. Nos. 3,641,235; 4,094,647 and 4,168,146). The devices described in such patents are generally considered difficult to manufacture and susceptible to irreproducibility due to the complex nature of the many chemical and physical interactions that take place along the carrier element during performance of an assay.

The application of homogeneous specific binding assay reagent systems to solid state test devices would provide great advantages to the routine user of such assay systems. The determination of ligands appearing in very low concentrations in liquid samples would be simplified to the steps of contacting the device with the sample and measuring, either by visual observation or by instrumental means, the resulting signal. Reagents would be provided in a solid form, with no need to store, dispense or mix liquid reagents as required when using the prior art test kits. Solid state devices would also be much more adaptable to automation than the prior art liquid systems.

The prior art lacks a detailed teaching of how to apply homogeneous specific binding assay reagent systems to solid state test devices. British Patent Spec. No. 1,552,607, commonly assigned herewith, describes homogeneous specific binding assay systems employing various novel labels, including chemiluminescent labels, enzyme substrate labels and coenzyme labels. At page 23, lines 12 et seq of this patent there is the suggestion of incorporating the assay reagents with various carriers including liquid-holding vessels or insoluble, porous, and preferably absorbent, matrices, fleeces, or blocks; gels; and the like.

German OLS No. 2,537,275 describes a homogeneous specific binding assay reagent system and poses the possibility of using slides or strips incorporated with antibody in performing the assay. In this suggestion, the label conjugate would be first mixed with the sample and thereafter the antibody incorporated test device contacted with the reaction mixture. After a suitable incubation time, it is proposed that the test device would be rinsed with buffer, dried, and then the signal (fluorescence) measured. Thus, this German OLS poses a test device and assay method much like those already known for heterogeneous specific binding assay techniques wherein the test device is immersed in the liquid reaction mixture, incubated, thereafter removed, washed, and finally read. Additionally, the proposed test device does not incorporate all of the binding assay reagents with the carrier element. Specifically, only the antibody is proposed to be incorporated with the carrier element with the label conjugate being separately added to the sample under assay prior to contact with the proposed test device.

Copending U.S. Ser. No. 255,521 filed on Apr. 20, 1981, and commonly assigned herewith, discloses a method for determining the presence of a ligand in, or the ligand binding capacity of, a liquid test sample. The method comprises the steps of adding to said liquid sample a label conjugate comprising said ligand, or a binding analogue thereof, chemically bound to a label, contacting said sample with a test device comprising a carrier matrix incorporated with reagents which, when combined with said label conjugate, produces a homogeneous specific binding assay system which results in a detectable response which is a function of the presence of said ligand or said ligand binding capacity, thereby producing said response, and measuring said response.

Copending U.S. Ser. No. 202,378, filed on Oct. 30, 1980, abandoned, and commonly assigned herewith, discloses a homogeneous specific binding assay device, a method for its preparation, and a method for its use in determining a ligand in, or the ligand binding capacity of, a liquid sample. This includes, for example, a test device for determining a ligand in or the ligand binding capacity of a liquid sample, comprising (a) reagents for a homogeneous specific binding assay system which produces a detectable response that is a function of the presence of the ligand in or the ligand binding capacity of the sample, and (b) a solid carrier member incorporated with said reagents.

Copending U.S. Ser. No. 253,147, filed on Apr. 10, 1981, and commonly assigned herewith, discloses a homogenèous specific binding assay device for use in determining a ligand in a liquid sample, comprising (a) a reagent composition including a complex of (i) a label conjugate comprising a label component coupled to said ligand or a specific binding analog thereof, and (ii) a specific binding partner for said ligand, said label providing a detectable response, or interacting with a detectant system to provide a detectable response, which is different when the label conjugate is bound by said binding partner compared to when it is not so bound and (b) a carrier incorporated with said complex.

Copending application U.S. Ser. No. 280,260 entitled "Homogeneous Specific Binding Assay Element and Method For Preventing Premature Reaction" filed on July 6, 1981, and commonly assigned herewith, discloses a homogeneous specific binding assay element, a method for its preparation, and a method for its use in determining a ligand in or the ligand binding capacity of a liquid sample. The test element comprises a solid carrier incorporated with reagents for a homogeneous specific binding assay system which produces a detectable response, usually an electromagnetic radiation signal, that is a function of the presence or amount of the ligand in or the ligand binding capacity of the sample. There is further disclosed a method for preparing a homogeneous specific binding assay element for determining a ligand in or the ligand binding capacity of a liquid sample by incorporating a carrier with a composition which includes a label conjugate, comprising a label component coupled to a ligand moiety or a specific binding analog thereof, and a reagent reactive with the label conjugate, which method comprises (a) incorporating the carrier with the reagent reactive with the label conjugate in a first liquid and drying the carrier; and then (b) incorporating the carrier of (a) with the label conjugate in a liquid effective to prevent reaction with the reagent reactive with the label conjugate prior to contact of the element with the sample and drying the carrier.

SUMMARY OF THE INVENTION

The present invention provides a homogeneous specific binding assay test element, a method for its preparation, and a method for its use in determining a ligand in or the ligand binding capacity of a liquid sample. The test element comprises (a) reagents for a homogeneous specific binding assay system which produces a detectable response that is a function of the presence, in a qualitative or quantitative sense, of the ligand in or the ligand binding capacity of the liquid sample under assay, and (b) a solid carrier incorporated with the reagents. Particularly, the invention provides a method for preparing a homogeneous specific binding assay element for determining a ligand in or the ligand binding capacity of a liquid sample by incorporating a carrier with a composition which includes a label conjugate, comprising a label component coupled to a ligand moiety or a specific binding analog thereof, and a reagent reactive with the label conjugate, which method comprises (a) incorporating the carrier with the reagent reactive with the label conjugate in a first liquid; (b) subjecting the carrier of (a) to conditions effective to reversibly suspend or reduce the activity of the reagent therein; (c) incorporating the carrier of (b) with the label conjugate; (d) subjecting the carrier of (c) to a temperature effective to freeze the reagent reactive with the label conjugate and the label conjugate; and (e) lyophilizing the reagent and label conjugate in the carrier of (d).

By precisely following the steps of the above defined method it is possible to incorporate all the reagent necessary for a specific binding assay into an integral single layer element.

DESCRIPTION OF THE PREFERRED EMBODIMENTS

The present invention provides a test device for use in carrying out homogeneous specific binding assays, e.g., immunoassays, having all of the convenience features of conventional analytical test strips and other test elements of similar design. As in the case of such conventional devices, the present invention provides a solid carrier, usually a matrix of one sort or another, incorporated with all of the reagents necessary to perform a given assay whereby the user has only the task of bringing the test device into contact with the sample to be tested and measuring the resulting response. Where the entire process is automated, an instrument for performing the same manipulations can have a much simpler design than one having a deal with conventional liquid chemistry systems now used for performing homogeneous specific binding assays.

1. HOMOGENEOUS SPECIFIC BINDING ASSAYS

Reagents for any homogeneous specific binding assay system can be incorporated in the present test device. In general, homogeneous specific binding assay techniques are based on the special interaction between (1) a conjugate of a binding component and a label and (2) a binding partner to the binding component in the conjugate, whereby a characteristic of the label is different when the label conjugate is bound by the binding partner compared to when such conjugate is not so bound. The affected characteristic of the label may be of any measurable nature, for instance, a chemical or physical quality of the label. In some cases, the affected characteristic is a chemical reactivity in a predetermined reaction which involves the formation or breaking of chemical bonds, covalent or noncovalent. In other cases, the affected characteristic is a physical characteristic of the label which can be measured without chemical reaction.

In the majority of cases, the present test device will incorporate homogeneous specific binding assay reagents which respond to the ligand or its binding capacity in the sample in an immunochemical manner. That is, there will be an antigen-antibody or hapten-antibody relationship between reagents and/or the ligand or its binding capacity in the sample. Such assays therefore are termed immunoassays and the special interaction between the label conjugate and its binding partner is an immunochemical binding. Thus, in such instances, the binding component of the label conjugate is an antigen, hapten or antibody (or a fragment thereof) and the binding partner is its corresponding immunochemical binding partner. However, it is well understood in the art that other binding interactions between the label conjugate and the binding partner serve as the basis of homogeneous specific binding assays, including the binding interactions between hormones, vitamins, metabolites, and pharmacological agents, and their respective receptors and binding substances.

Where the sample is being assayed to determine the presence or amount of a particular ligand therein, the reagents for the homogeneous specific binding assay technique comprise, in the usual case, (1) a label conjugate composed of the ligand, or a binding analog thereof, chemically coupled to the label, (2) a binding partner for the ligand, e.g., an antibody or fragment thereof, a natural receptor protein, and the like, and (3) any ancillary reagents necessary for measuring the labeling substance in the label conjugate. A limiting amount of the binding partner is introduced so that any ligand in the sample will compete with the label conjugate for binding to the binding partner. The distribution of the label between the bound-species and the free-species will therefore determine the magnitude of the detectable response from the label, which in turn will be a function of the presence of the ligand. Another scheme for determining a ligand is presented where the label conjugate is composed of a labeled binding partner of the ligand and, upon binding to the ligand, the label is affected in terms of its detectable response. Where ligand binding capacity of the sample is under assay, the label conjugate will be composed of the ligand, or a binding analog thereof, chemically coupled to the label whereby the capacity of the sample to bind the label conjugate, such as due to the presence of a binding partner of the ligand in the sample, determines the effect made on the detectable signal from the label.

Several different homogeneous specific binding assay systems are known in the art, and the following are examples, without limiting the scope of the present invention, of some such systems contemplated for use in the present test device. The following systems are listed according to the nature of the label used.

(a) Enzyme Prosthetic Group Labels

In this system, where the label is a prosthetic group of an enzyme, the ability of a catalytically inactive apoenzyme to combine with the prosthetic group label to form an active enzyme (haloenzyme) is affected by binding of the label conjugate with its binding partner.

Resulting holoenzyme activity is measurable by conventional detectant systems to yield an ultimately detectable signal. Assay systems of this type are described in commonly assigned, copending application Ser. No. 45,423, filed June 4, 1979, Pat. No. 4,238,565, (corresponding to published British Patent Spec. No. 2,023,607). A particularly preferred prosthetic group-label assay scheme employs flavin adenine dinucleotide (FAD) as the label and apoglucose oxidase as the apoenzyme. Resulting glucose oxidase activity is measurable by a colorimetric detectant system comprising glucose, peroxidase, and an indicator system which produces a color change in response to hydrogen peroxide.

In such preferred assay scheme, the FAD-labeled conjugate is preferably of the formula:

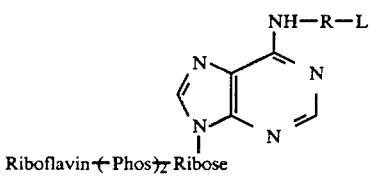

wherein Riboflavin—Phos)$_2$ Ribose represents the riboflavin-pyrophosphate-ribose residue in FAD, R is a linking group, and L is the binding component, e.g., the ligand or analog thereof.

(b) Enzyme Substrate Labels

In this system, the label is selected so that the label conjugate is a substrate for an enzyme and the ability of the enzyme to act on the substrate-label conjugate is affected, either in a positive or negative sense, by binding of the label conjugate with its binding partner. Action of the enzyme on the substrate-label conjugate produces a product that is distinguishable in some feature, usually a chemical or physical feature such as chemical reactivity in an indicator reaction or such as a photometric character, e.g., fluorescence or light absorption (color). Assay systems of this type are described in commonly assigned, copending application Ser. Nos. 894,836, filed Apr. 10, 1978 (corresponding to published German OLS No. 2,618,511) and 87,819, filed Oct. 23, 1979, Pat. No. 4,279,992; and in Anal. Chem. 48:1933 (1976), Anal. Biochem. 77:55 (1977) and Clin. Chem. 23:1402 (1977). A particularly preferred substrate-label assay scheme employs a label conjugate of the structure

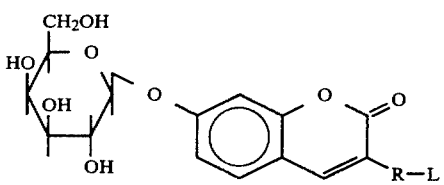

wherein R is a linking group and L is the binding component, e.g., the ligand or analog thereof, whereby the ability of the enzyme β-galactosidase to cleave the conjugate yielding a product distinguishable by its fluorescence is inhibited by binding of the conjugate with its binding partner.

An important application of this technique is in aminoglycoside antibiotic assays wherein the binding component is the antibiotic under assay or a binding analog thereof. In assays where antibody is used as the binding partner it has been found that other aminoglycoside antibiotics can cross-react with the antibody for the antibiotic under assay. Thus, such other antibiotics qualify as binding analogs and may be used to form the label conjugate. Further, the antibody qualifies as a reagent for use in assays for the cross-reacting antibiotic. For example, in an assay for gentamicin it has been found that, with an appropriate antiserum, the binding component in the label conjugate can be gentamicin itself or sisomicin which cross-reacts. Thus, gentamicin antiserum and a labeled sisomicin conjugate could be used in an assay for gentamicin. Specificity problems are not encountered in clinical situations because it would be known what antibiotic was administered and only one aminoglycoside antibiotic is administered at a time.

The β-galactosyl-umbelliferone-label conjugates formed are of the formula:

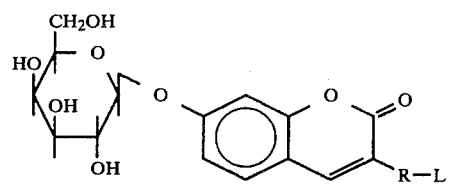

wherein R is a linking group terminating in an amino-linking group, preferably carbonyl and L is an aminoglycoside antibiotic coupled by a covalent bond to the linking group R through a primary amino group therein.

(c) Coenzyme Labels

The label conjugate in this system is composed in its label portion, by a coenzyme-active functionality. The ability of the coenzyme label to participate in an enzymatic reaction is affected by binding of the label conjugate with its binding partner. The rate of the resulting enzymatic reaction is measurable by conventional detectant systems to yield an ultimately detectable signal. Assay systems of this type are described in commonly assigned, copending application Ser. No. 894,836, filed Apr. 10, 1978 (corresponding to published German OLS No. 2,618,511); and in Anal. Biochem. 72:271 (1976), Anal. Biochem. 72:283 (1976) and Anal. Biochem. 76:95 (1976).

(d) Enzyme Modulator Labels

The label conjugate in this system is composed, in its label portion, of an enzyme modulating functionality such as an enzyme inhibitor or stimulator. The ability of the modulator label to modulate the activity of an enzyme is affected by binding of the label conjugate with its binding partner. The rate of the resulting enzymatic reaction is measurable by conventional detectant systems to yield an ultimately detectable signal. Assay systems of this type are described in commonly owned U.S. Pat. No. 4,134,792.

(e) Enzyme Labels

In this system, the label is an enzyme and the activity of the enzyme label is affected by binding of the label conjugate with its binding partner. Resulting enzyme activity is measurable by conventional detectant systems to yield an ultimately detectable signal. Assay systems of this type are described in U.S. Pat. Nos. 3,817,837 and 4,043,872.

(f) Quenchable Fluorescent Labels

The label conjugate in this system is composed in its label portion, of a fluor the fluorescence of which is quenched in some measurable degree when the label conjugate is bound by its binding partner, usually a protein such as an antibody. The fluorescent label is measured directly, with its fluorescence being the detectable signal. Assay systems of this type are described in U.S. Pat. No. 4,160,016 and in J. Clin. Path. 30:526 (1977).

(g) Chemically-Excited Fluorescent Labels

In this system, the label is again a fluor, however, the ability of the fluor label to be chemically excited to an energy state at which it fluoresces is affected by binding of the label conjugate with its binding partner. Chemical excitation of the label is usually accomplished by exposure of the fluor label to a high energy compound formed in situ. Assay systems of this type are described in commonly-owned, copending application Ser. No. 4,580, filed Jan. 18, 1979, Pat. No. 4,238,195.

(h) Double Antibody Steric Hindrance Labels

Another assay system is the double antibody immunoassay system described in U.S. Pat. Nos. 3,935,074 and 3,998,943. The label conjugate comprises two epitopes, one of which participates in the immunological reaction with the ligand and antiligand antibody and the other of which is bindable by a second antibody, with the restriction that the two antibodies are hindered from binding to the label conjugate simultaneously. The second epitope can be a fluorescent substance the fluorescence of which is quenched by the second antibody binding, or may participate in an ancillary competitive binding reaction with a labeled form of the second epitope for binding to the second antibody. Various detectant systems are possible in such a system as described in the aforementioned patents. Related assay systems are described in U.S. Pat. Nos. 4,130,462 and 4,161,515 and in British Pat. Spec. No. 1,560,852.

(i) Energy Transfer Labels

In this system, the label is one member of an energy transfer donor-acceptor pair and the binding partner is conjugated with the other of such pair. Thus, when the label conjugate is bound by its binding partner, the energy expression of the donor component of the pair is altered by transferance to the acceptor component. Usually, the donor is a fluor and the acceptor is a quencher therefor, which quencher may or may not be a fluor as well. In such embodiment, the detectable signal is fluorescence, but other detectant systems are possible also. Such assay systems are described in U.S. Pat. Nos. 3,996,345; 4,174,384; and 4,199,559 and in British Pat. Spec. No. 2,018,424.

(j) Other Labels

Other homogeneous specific binding assay systems described in the art which can be used in the present invention include the use of labels such as:
(i) nonenzymic catalysts, such as electron transfer agents (see U.S. Pat. No. 4,160,645);
(ii) nonenzymic chemiluminescers (see commonly owned, copending application Ser. No. 894,836 referred to above);
(iii) "channeling" labels (see British Pat. Spec. No. 2,018,986);
(iv) "particle" labels (see British Pat. Spec. No. 2,019,562); and
(v) labeled liposome particles (see U.S. Pat. No. 4,193,983).

2. LIGAND

The present assay can be applied to the detection of any ligand for which there is a specific binding partner and, conversely, to the detection of the capacity of a liquid medium to bind a ligand (usually due to the presence of a binding partner for the ligand in the medium). The ligand usually is a peptide, polypeptide, protein, carbohydrate, glycoprotein, steroid, or other organic molecule for which a specific binding partner exists in biological systems or can be synthesized. The ligand, in functional terms, is usually selected from the group comprising antigens and antibodies thereto; haptens and antibodies thereto; and hormones, vitamins, metabolites and pharmacological agents, and their receptors and binding substances. Usually, the ligand is an immunologically-active polypeptide or protein of molecular weight between 1,000 and 10,000,000, such as an antibody or antigenic polypeptide or protein, or a hapten of molecular weight between 100 and 1,500.

Representative polypeptide ligands are angiotensin I and II, C-peptide, oxytocin, vasopressin, neurophysin, gastrin, secretin, bradykinin, and glucagon.

Representative protein ligands include the classes of protamines, mucoproteins, glycoproteins, globulins, albumins, scleroproteins, phosphoproteins, histones, lipoproteins, chromoproteins, and nucleoproteins. Examples of specific proteins are prealbumin, $\alpha_1$-lipoprotein, human serum albumin, $\alpha_1$-glycoprotein, transcortin, thyroxine binding globulin, haptoglobin, hemoglobin, myoglobin, ceruloplasmin, $\alpha_2$-lipoprotein, $\alpha_2$-macroglobulin, $\beta$-lipoprotein, erythropoietin, transferrin, homopexin, fibrinogen, the immunoglobulins such as IgG, IgM, IgA, IgD, and IgE, and their fragments, e.g., $F_c$ and $F_{ab}$, complement factors, prolactin, blood clotting factors such as fibrionogen, thrombin and so forth, insulin, melanotropin, somatotropin, thyrotropin, follicle stimulating hormone, leutinizing hormone, gonadotropin, thyroid stimulating hormone, placental lactogen, intrinsic factor, transcobalamin, serum enzymes such as alkaline phosphatase, lactic dehydrogenase, amylase, lipase, phosphatases, cholinesterase, glutamic oxaloacetic transaminase, glutamic pyruvic transaminase, and uropepsin, endorphins, enkephalins, protamine, tissue antigens, bacterial antigens, and viral antigens such as hepatitis associated antigens (e.g., $HB_sAg$, $HB_cAg$ and $HB_eAg$).

Representative hapten ligands include the general classes of drugs, metabolites, hormones, vitamins, and the like organic compounds. Haptenic hormones include vitamins A, B, e.g., $B_{12}$, C, D, E, and K, folic acid and thiamine. Drugs include antibiotics such as aminoglycosides, e.g., gentamicin, tobramycin, amikacin, sisomicin, kanamycin, and netilimicin, penicillin, tetracycline, terramycin, chloromycetin, and actinomycetin; nucleosides and nucleotides such as adenosine diphosphate (ADP), adenosine triphosphate (ATP), flavin mononucleotide (FMN), nicotinamide adenine dinucleotide (NAD) and its phosphate derivative (NADP), thymidine, guanosine and adenosine; prostaglandins; steroids such as the estrogens, e.g., estriol and estradiol, sterogens, androgens, digoxin, digitoxin, and adrenocortical steroids; and others such as phenobarbital, phenyltoin, primidone, ethosuximide, carbamazepine, valproate, theophylline, caffeine, propranolol, procainamide, quinidine, amitryptiline, cortisol, desipramine, disopyramide, doxepine, doxorubicin, nortryptiline, methotrexate, imipramine, lidocaine, procainamide, N-acetylprocainamide, the amphetamines, the catecholamines, and the antihistamines.

The liquid medium to be assayed can be a naturally occurring or artificially formed liquid suspected to contain the ligand, and usually is a biological fluid or a dilution thereof. Biological fluids that can be assayed include serum, plasma, urine, saliva, and amniotic and cerebrospinal fluids.

3. CARRIER MEMBER

The carrier member of the present invention can take on a multitude of forms, and is therefore intended as being broad in context. It can be mono- or multi-phasic, comprising one or more appropriate materials or mediums of similar or different absorptive or other physical characteristics. It can be hydrophobic or hydrophilic, bibulous or nonporous. In its most efficient embodiment the carrier member can be carefully tailored to suit the characteristics of the particular homogeneous specific binding assay system to be employed.

Thus, as used herein, the term "carrier member" can comprise any substance, matrix, or surface capable of being incorporated with specific binding assay reagents. It can take on many known forms such as those utilized for chemical and enzymatic reagent strips for solution analysis. For example, U.S. Pat. No. 3,846,247 teaches the use of felt, porous ceramic strips, and woven or matted glass fibers. As substitutes for paper, U.S. Pat. No. 3,552,928 teaches the use of wood sticks, cloth, sponge material, and argillaceous substances. The use of synthetic resin fleeces and glass fiber felts in place of papers is suggested in British Pat. No. 1,369,139. Another British Pat. No. 1,349,623, suggests the use of a light-permeable meshwork of thin filaments as a cover for an underlying paper carrier element. This reference also suggests impregnating the paper with part of a reagent system and impregnating the meshwork with other potentially incompatible chemical or enzymatic reagents. French Pat. No. 2,170,397 teaches the use of carrier members having greater than 50% polyamide fibers therein. U.S. Pat. No. 4,046,514 discloses the interweaving or knitting of filaments bearing reagents in a reactant system. All such carrier member concepts can be employed in the present invention, as can others. Preferably the carrier member comprises a bibulous material, such as filter paper, whereby a solution or suspension of the reagents of the specific binding assay system is used to impregnate the carrier member. It can comprise a system wherein the ingredients are homogeneously combined with the carrier member in a fluid or semi-fluid state, which later hardens or sets, thereby entrapping the ingredients.

Whichever material is chosen for the carrier member, whether it be porous to permit incorporation of ingredients such as through saturation with a solution containing them, whether it be nonporous such as to support or create a continuous coating, whether it be woven or knitted, whatever its composition or configuration, its selection will in any event be dictated by anticipated use and by the reagent system.

4. PREPARATION OF THE TEST DEVICE

A method of preparing the test device is provided by the present invention. This is a method for preparing a homogeneous specific binding assay element for determining a ligand in or the ligand binding capacity of a liquid sample by incorporating a carrier with a composition which includes a label conjugate, comprising a label component coupled to a ligand moiety or a specific binding analog thereof, and a reagent reactive with the label conjugate, which method comprises (a) incorporating the carrier with the reagent reactive with the label conjugate in a first liquid; (b) subjecting the carrier of (a) to conditions effective to reversibly suspend or reduce the activity of the reagent therein; (c) incorporating the carrier of (b) with the label conjugate; (d) subjecting the carrier of (c) to a temperature effective to freeze the reagent reactive with the label conjugate and the label conjugate; and (e) lyophilizing the reagent and label conjugate in the carrier of (d).

By lyophilization, the need for frozen storage can be avoided by allowing the ice in the frozen substance to sublime. In addition removal of water prevents reaction between species which would otherwise interact in aqueous media. This will leave a dry, porous solid residue which can be stored at room temperature until reconstituted for use by adding an aqueous sample such as a body fluid. If this process is properly carried out the final product will have the same size and shape as when frozen. It will be easily dissolved in water, that is, lyophilic—hence lyophilization—a synonym for freeze-drying.

In general the product for lyophilization should be brought below the eutectic temperature of this material prior to application of vacuum. For aqueous samples, a temperature of less than $-40°$ Farenheit (F.) will ensure adequate freezing. This can be accomplished by application of the device to dry ice, immersion of the device into a dry ice-acetone bath or application of the device to freezing surfaces available in many commercial freeze drying devices. The vacuum applied to the sample should be sufficient to ensure removal of water by sublimation. Vacuum of 50 microns of mercury or less will be effective for such a purpose.

For many years the standard work on freeze-drying was by Flosdorf [Flosdorf, E. W., Freeze-Drying, Reinhold Publishing Corp., New York (1949)]. Most of the different aspects involved in the process are discussed at length in books edited by Harris [Harris, R. J. C. (ed.), Biological Applications of Freezing and Drying, Academic Press, New York (1954)] and Parkes and Smith [Parkes, A. S. and Smith A. U. (eds.), Recent Research in Freezing and Drying, Blackwell, Oxford (1960)]. A condensed review by Meryman [Meryman, H. T., "Freeze-Drying", (Meryman, H. T., ed.) in Cryobiology, pp. 609–663, Academic Press, New York (1966)] gives prominence to biological aspects.

The reactive reagent can comprise, for example, a specific binding partner for the ligand or a specific binding partner for the ligand and a component which is reactive with the label conjugate to cleave the label component from the ligand moiety or specific binding analog thereof.

Where the carrier comprises additional layers, e.g., paper or other fibrous material, such layers can be maintained in laminar relationship by adhesives which permit fluid passage between layers. In preparing integral analytical elements using film formers, the additional layer(s) can be preformed separately and laminated to form the overall element. The material of the film layer(s) can be a composition comprising a plasticizer and a polymer suitable to impart dimensional stability. Layers prepared in such a manner are typically coated from solution or dispersion onto a surface from which the dried layer can be physically stripped. However, a convenient method which can avoid problems of multiple stripping and lamination steps is to coat an initial layer on a stripping surface or a support, as desired, and thereafter to coat successive layers directly on those coated previously. Such coatings can be accomplished by hand, using a blade coating device, or by machine, using techniques such as dip or bead coating. In machine coating techniques are used, it is often possible to coat adjacent layers simultaneously using hopper coating techniques well known in the preparation of light sensitive photographic films and papers.

The thickness of any layer and its degree of permeability are widely variable and depend on actual usage. Dry thickness of from about 5 microns to 100 microns have been convenient, although more widely varying thickness may be preferable in certain circumstances. For example, if comparatively large amounts of interactive material, e.g., polymeric materials like enzymes, are required, it may be desirable to prepare slightly thicker layers.

It can also be desirable to include within a carrier one or more reflective layers, optionally absorptive to detecting radiation, such as to facilitate signal detection by reflection radiometry, e.g., reflection photometry or a similar technique. Such reflector can be provided by one of the above-described layers or it can be provided by an additional layer that may not have an additional function within the element. Reflective pigments, such as titanium dioxide and barium sulfate, can be used to advantage in a reflecting layer. Blush polymers can also constitute a suitable reflecting material. In one preferred aspect, blush polymer layers can also incorporate a pigment to enhance reflectivity or other functions. The amount of pigment that can be included in a layer together with a blush polymer is highly variable, and amounts of from about 1 to about 10 parts by weight of pigment per part by weight of blush polymer are preferred, with from about 3 to about 6 parts pigment per part of blush polymer being most preferred.

It can be advantageous to incorporate one or more surfactant materials, such as anionic and nonionic surfactant materials, in the layers of the carrier. They can, for example, enhance coatability of layers formulations and enhance the extent and range of wetting in layers that are not easily wetted by liquid samples in the absence of an aid such as a surfactant.

As mentioned previously herein, the integral analytical elements can be self-supporting or mounted on a support. The support can be opaque or transparent to light or other energy. A support of choice for any particular carrier will be compatible with the intended mode of signal detection. Preferred supports include transparent support materials capable of transmitting electromagnetic radiation of a wavelength within the region between about 200 nanometers (nm) and about 900 nm. The support need not, of course, transmit over the entire 200–900 nm region, although for fluorometric detection of analytical results through the support it is desirable for the support to transmit over a wider band or, alternatively, to transmit at the absorption and emission spectra of the fluorescent materials used for detection. It may also be desirable to have a support that transmits one or more narrow wavelength bands and is opaque to adjacent wavelength bands. This could be accomplished, for example, by impregnating or coating the support with one or more colorants having suitable absorption characteristics.

5. DETECTABLE RESPONSE

As previously noted, many of the recently devised homogeneous specific binding assay systems provide, or can be readily adapted to provide, a detectable response such as a color change, chemiluminescence, or fluorescence related to the presence or amount of the ligand under assay in the liquid sample.

The expression "detectable species", and similar expressions as used herein, refer to atoms, chemical groups (i.e., a portion of a molecule) or chemical compounds that are themselves directly or indirectly detectable and the expression "detectable response", and similar expressions as used herein, refer to the detectable manifestation of the presence of such species. Examples are electromagnetic radiation signals such as fluorescence, phosphorescence, chemiluminescence, a change in light absorption, or reflectance in the visible spectrum thereby producing a visible color change, a change in light absorption or reflectance outside the visible range, such as in the ultraviolet or infrared range. As will be apparent to one skilled in the art of specific binding assays, the phrase "detectable response", as used herein, is intended in its broadest sense. In addition to electromagnetic radiations signals the expression "detectable response" is also meant to include any observable change in a system parameter, such as a change in or appearance of a reactant, observable precipitation of any component in the test sample or a change in any other parameter, whether it be in the assay system or the test sample. Such other detectable responses include electrochemical responses and calorimetric responses. Moreover, the detectable response is one which can be observed through the senses directly or by use of ancillary detection means, such as a spectrophotometer, ultraviolet light-sensing equipment, fluorometer, spectrofluorometer, pH meter or other sensing means.

After the analytical result is obtained as a detectable change, it is measured, usually by passing the test element through a zone in which suitable apparatus for reflection, transmission or fluorescence photometry is provided. Such apparatus serves to direct a beam of energy, such as light, at the element. The light is then reflected from the element back to a detecting means or passes through the element to a detector in the case of transmission detection. In a preferred mode, the analytical result is detected in a region of the element totally within the region in which such result is produced. Use of reflection spectrophotometry can be advantageous in some situations as it effectively avoids optical interference from many residues, such as blood cells or urine sediment, which have been left on or in the layers of the element or from atypical urine colors. Conventional techniques of fluorescence spectrophotometry can also be employed if desired. Furthermore, transmission techniques can be used to detect and quantify the indicating reaction products by reacting a flow of radiant energy, for example, ultraviolet, visible or infrared radiation at one surface of the element and measuring the output of that energy from the opposing surface of the element. Generally, electromagnetic radiation in the range of from about 200 to about 900 nm has been found useful for such measurements, although any radiation to which the element is permeable and which is capable of quantifying the product produced in the element can be used. Various calibration techniques can be used to provide a control for the analysis. As one example, a sample of a standard solution of the ligand under assay can be applied adjacent to the area where the drop of sample is placed in order to permit the use of differential measurements in the analysis.

EXAMPLES

The following examples describe experiments which were performed in developing the present invention. While they illustrate preferred embodiments, they are in no way to be interpreted as limiting the scope of the invention.

EXAMPLE I

Analytical Element for Colorimetric Determination of Theophylline

Theophylline [1,3-dimethylxanthine, cf. The Merck Index, 9th ed., p. 1196 (1976)] is a drug useful in the management of asthma. In most patients, the therapeutic range of serum concentration lies between 10 and 20 micrograms/milliliter ($\mu$g/ml) whereas toxicity almost invariably appears at blood levels over 35 $\mu$g/ml.

Element Preparation

Segments of Whatman 31ET filter paper (Whatman Co., Clifton, N.J.), 0.5 centimeters (cm)×1 cm, were mounted on strips of Trycite ® polystyrene film (3M Company, St. Paul, Minn.) and impregnated with 20 microliters ($\mu$l) of a solution having the following formulation:

| | |
|---|---|
| 0.5 M Bicine[1] buffer, pH 8.5 | 10 $\mu$l |
| $\beta$-galactosidase (83 IU/ml) | 40 $\mu$l |
| theophylline antisera concentrate[2] | 150 $\mu$l |

[1]Bicine is N,N—bis[2-hydroxyethyl]glycine
[2]Approximately 200 $\mu$moles of theophylline binding sites/ml, prepared from an ammonium sulfate (33%) precipitate of theophylline antisera, dissolved and dialyzed vs 0.05 M Bicine, pH 8.5. The quantity is adjusted to minimize the reaction upon addition of theophylline-umbelliferone-galactose.

These mounted and impregnated segments were dried for fifteen (15) minutes at 50 degrees centigrade (C). They were precooled on dry ice for five (5) minutes in a low humidity room.

A 6.13 millimolar (mM) solution of theophylline-umbelliferone-galactose conjugate in dimethylsulfoxide was diluted to a 0.15 mM solution with water and 20 $\mu$l was applied to each segment. They were then rapidly frozen on dry ice and then freeze-dried overnight, thus providing analytical elements according to the invention.

Analytical Procedure

Hydrolysis of the theophylline-umbelliferone-galactose conjugate releases theophylline-umbelliferone which has an absorption maximum at about 400 nanometers (nm). Response was measured in a Seralyzer ® reflectance photometer (Miles Laboratories, Inc., Elkhart, Ind.). Reflectance (R) changes were followed at 400 nanometers (nm) and the values were converted to the Kubelka Munk ratio (K/S), where $K/S = (1-R)^2/2R$.

Results

As shown in Table 1, the reaction is inhibited by the presence of antisera and this inhibition can be progressively overcome by increasing concentrations of theophylline (reported as $\mu$g/ml).

TABLE 1

| Theophylline | K/S at 300 seconds |
|---|---|
| 0 | 0.546 |
| 1 | 0.605 |
| 2 | 0.632 |
| 4 | 0.685 |
| 8 | 0.712 |
| 16 | 0.735 |
| 40 | 0.835 |

Conclusion

The results demonstrate that all reagents necessary for colorimetric determination of theophylline can be incorporated into a single element layer while minimizing premature reaction by application of a freeze-drying procedure. A dose dependent response is likewise demonstrated.

EXAMPLE II

Analytical Element for Fluorescent Determination of Theophylline

The elements prepared and tested as described in this example are used to perform a substrate-labeled fluorescent immunoassay for the quantitative determination of theophylline.

Element Preparation

Segments of Whatman 31ET filter paper, 1 cm×1 cm were mounted on Trycite ® film and impregnated with 50 $\mu$l of a solution having the following formulation:

| | |
|---|---|
| 0.5 M Bicine buffer, pH 8.5 | 72 $\mu$l |
| $\beta$-galactosidase (83 I.U./ml) | 12 $\mu$l |
| Theophylline antisera | 396 $\mu$l |
| H$_2$O | 120 $\mu$l |

The enzyme activity is expressed in International Units (I.U.), one I.U. being the amount of enzyme activity required to catalyze the conversion of 1 micromole ($\mu$mol) of substrate per minute under specified conditions of pH and temperature. These mounted and impregnated segments pads were dried for fifteen (15) minutes at 50 degrees Centigrade (C). The segments were precooled on dry ice for five (5) minutes prior to application of conjugate.

A 6.13 mM solution of theophylline-umbelliferone-galactose conjugate in dimethylsulfoxide was diluted to 8.5 micromolar ($\mu$M) in water and cooled on ice. Thirty (30) $\mu$l was applied to each segment. Each segment was frozen and then was lyophilized overnight to provide test devices according to the invention.

Analytical Procedure & Results

Fluorescence was measured using a modified SLM 8000 Photon Counting Spectrofluorometer (SLM Instruments, Inc. Urbana, IL). The instrument was modified by introduction of a mechanical holder for the analytical element to be read. The element is held stationary in a vertical position. The fluorometer had been adjusted to provide an excitation light source of 405 nm wavelength, which struck the surface of the element at a 60° angle from normal, and to detect light emitted at a wavelength of 450 nm. A front face measurement of fluorescence was made at a 30° angle from the normal to the pad.

Reaction was initiated by the application of 60 μl of sample containing theophylline in 0.1M Bicine, pH 8.5 to the element. Thereafter the element was inserted into the holder which was positioned in the instrument. The response over a range of theophylline concentrations from 0 μg/ml (microgram per milliliter) to 16 μg/ml was measured at 120 seconds. The results are shown in Table 2 where fluorescence response is in arbitrary units.

TABLE 2

| Theophylline | Fluorescence |
| --- | --- |
| 0 | 170 |
| .5 | 225 |
| 1 | 240 |
| 2 | 275 |
| 4 | 350 |
| 8 | 360 |
| 16 | 405 |

Conclusion

The results demonstrate that all reagents of a substrate labeled fluorescence immunoassay can be incorporated into a single paper pad while minimizing premature reaction by application of a freeze-drying procedure. A dose dependent response is likewise demonstrated.

What is claimed is:

1. A test device for determining a ligand in, or the ligand binding capacity of, a test sample, the device comprising
    a support member having a substantially planar side,
    a carrier member affixed to the substantially planar side, the carrier member comprising a substantially bibulous material, and
    a reagent system homogeneously incorporated with, but not bound to, the carrier member, the reagent system comprising ingredients capable of participating in a specific binding assay and including a label conjugate and a specific binding partner to the conjugate and the ligand, the conjugate comprising a label bound to the ligand or a specific binding analogue thereof, the conjugate and specific binding partner therefor being present in the carrier substantially unbound to one another.

2. The test device of claim 1 in which the label conjugate is a fluor bound to the ligand or specific binding analogue thereof.

3. The test device of claim 1 in which the label conjugate is unbelliferone-ligand.

4. The test device of claim 1 in which the reagent system additionally includes a component capable of cleaving the label from the conjugate.

5. The test device of claim 4 in which the label is an enzyme substrate and the compound is an enzyme reactive with the substrate.

6. The test device of claim 5 in which the label is a β-galactoside moiety and the enzyme is β-galactosidase.

7. The test device of claim 6 in which the label conjugate is β-galactosyl-umbelliferone-ligand or specific binding analogue thereof.

8. A method for preparing a test device for determining a ligand in, or the ligand binding capacity of, a test sample, the method comprising the sequential steps of
    incorporating a carrier member with a reagent system in a first solvent, the reagent system being capable of producing a detectable response to the presence of a label conjugate, and including a specific binding partner to the conjugate and a component capable of cleaving the label from the conjugate to produce a detectable response,
    drying the carrier member, to remove the first solvent
    cooling the dried carrier member to a temperature sufficient to substantially prevent the component from cleaving the label,
    further incorporating the carrier member with the label conjugate in a second solvent, the conjugate comprising the label coupled to the ligand or specific binding analogue thereof, the label being a moiety cleavable by the component to produce a detectable response,
    cooling the carrier member to a temperature sufficient to freeze the second solvent at a rate sufficient to prevent substantial cleavage of the label by the component, and lyophilizing the carrier member.

9. The method of claim 8 in which the label is a substrate for an enzyme, and the component is the enzyme for which the label is a substrate.

10. The method of claim 8 in which the ligand is theophylline, the label conjugate is theophylline-umbelliferone-galactose, the component is β-galactosidase and the specific binding partner is antibody to theophylline.

11. The method of claim 8 in which the label is a β-galactoside moiety and the component is β-galactosidase.

12. The method of claim 11 in which the label conjugate is β-galactosyl-umbelliferone-ligand or ligand binding analogue.

* * * * *